United States Patent
Mort et al.

(10) Patent No.: US 10,524,939 B2
(45) Date of Patent: Jan. 7, 2020

(54) IMPLANTABLE MEDICAL DEVICE WITH REDUCED MIGRATION CAPABILITIES

(71) Applicant: BOSTON SCIENTIFIC SCIMED, INC., Maple Grove, MN (US)

(72) Inventors: Paul G. Mort, Westborough, MA (US); Paul Mannion, Shrewsbury, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 336 days.

(21) Appl. No.: 14/996,164

(22) Filed: Jan. 14, 2016

(65) Prior Publication Data

US 2016/0206449 A1 Jul. 21, 2016

Related U.S. Application Data

(60) Provisional application No. 62/104,356, filed on Jan. 16, 2015.

(51) Int. Cl.
*A61F 2/04* (2013.01)
*A61F 2/86* (2013.01)
*A61F 2/95* (2013.01)

(52) U.S. Cl.
CPC .............. *A61F 2/86* (2013.01); *A61F 2/04* (2013.01); *A61F 2002/9528* (2013.01)

(58) Field of Classification Search
CPC ...... A61F 2/04; A61F 2/07; A61F 2/82; A61F 2/86; A61F 2/90; A61F 2002/9528
See application file for complete search history.

(56) References Cited

U.S. PATENT DOCUMENTS

| | | | |
|---|---|---|---|
| 5,035,706 A | 7/1991 | Giantureo et al. | |
| 5,238,004 A | 8/1993 | Sahatjian et al. | |
| 5,405,378 A | 4/1995 | Stecker | |
| 5,514,176 A | 5/1996 | Bosley, Jr. | |
| 5,662,713 A | 9/1997 | Andersen et al. | |
| 6,083,257 A * | 7/2000 | Taylor .................. | A61F 2/90 623/1.46 |
| 6,221,099 B1 | 4/2001 | Andersen et al. | |
| 6,355,070 B1 | 3/2002 | Andersen et al. | |
| 6,485,515 B2 | 11/2002 | Strecker | |
| 6,505,654 B1 | 1/2003 | Andersen et al. | |
| 6,508,803 B1 | 1/2003 | Horikawa et al. | |

(Continued)

FOREIGN PATENT DOCUMENTS

EP 0481365 A1 4/1992
JP 2007513743 A 5/2007
(Continued)

*Primary Examiner* — Dinah Baria
(74) *Attorney, Agent, or Firm* — Seager, Tufte & Wickhem, LLP

(57) ABSTRACT

Medical devices and methods for making and using a medical device are disclosed. An example medical device may include an implantable medical device. The implantable medical device may include a stent having a covered portion and an uncovered portion. The covered portion may be releasably attached to the uncovered portion. A cover member may be disposed along the covered portion. The uncovered portion may include a release tab that is designed to release the uncovered portion from the covered portion. A removal member may be coupled to the covered portion for aiding in the removal of the covered portion from an implantation site.

18 Claims, 6 Drawing Sheets

(56) References Cited

U.S. PATENT DOCUMENTS

| | | | |
|---|---|---|---|
| 6,821,291 B2 | 11/2004 | Bolea et al. | |
| 7,547,321 B2 | 6/2009 | Silvestri et al. | |
| 7,682,381 B2 | 3/2010 | Rakos et al. | |
| 7,815,589 B2 | 10/2010 | Meade et al. | |
| 7,875,068 B2 | 1/2011 | Mangiardi et al. | |
| 8,057,420 B2 | 11/2011 | Meade et al. | |
| 8,197,529 B2 | 6/2012 | Cully et al. | |
| 8,398,699 B2 | 3/2013 | Shin et al. | |
| 8,414,635 B2 | 4/2013 | Hyodoh et al. | |
| 8,491,647 B2 | 7/2013 | Colgan et al. | |
| 8,663,541 B2 | 3/2014 | Chun et al. | |
| 8,696,736 B2 | 4/2014 | Yachia et al. | |
| 8,739,382 B2 | 6/2014 | Sheldon et al. | |
| 8,753,407 B2 | 6/2014 | Nguyen | |
| 8,771,219 B2 | 7/2014 | Meade et al. | |
| 2002/0052649 A1 | 5/2002 | Greenhalgh | |
| 2003/0120332 A1 | 6/2003 | Hartley | |
| 2004/0176832 A1* | 9/2004 | Hartley | A61F 2/07 623/1.11 |
| 2007/0055364 A1* | 3/2007 | Hossainy | A61F 2/82 623/1.38 |
| 2011/0087146 A1* | 4/2011 | Ryan | A61F 2/04 604/8 |
| 2011/0245851 A1 | 10/2011 | Ducharme et al. | |
| 2012/0143306 A1 | 6/2012 | Cully et al. | |
| 2012/0158122 A1 | 6/2012 | Mattson et al. | |
| 2012/0283811 A1 | 11/2012 | Neilan | |
| 2013/0018215 A1 | 1/2013 | Snider et al. | |
| 2015/0282922 A1 | 10/2015 | Hingston et al. | |
| 2015/0282960 A1 | 10/2015 | Harris | |

FOREIGN PATENT DOCUMENTS

| | | |
|---|---|---|
| JP | 2014014709 A | 1/2014 |
| WO | 9401056 A1 | 1/1994 |
| WO | 0042949 A2 | 7/2000 |
| WO | 2005058201 A1 | 6/2005 |
| WO | 2005115275 A1 | 12/2005 |
| WO | 2006124541 A2 | 11/2006 |
| WO | 2008127551 A1 | 10/2008 |
| WO | 2011056638 A1 | 5/2011 |

* cited by examiner

IMPLANTABLE MEDICAL DEVICE WITH REDUCED MIGRATION CAPABILITIES

CROSS-REFERENCE TO RELATED APPLICATIONS

This application claims priority under 35 U.S.C. § 119(e) to U.S. Provisional Application No. 62/104,356, filed Jan. 16, 2015, the entire disclosure of which is herein incorporated by reference.

TECHNICAL FIELD

The present disclosure pertains to medical devices, and methods for manufacturing medical devices. More particularly, the present disclosure pertains to elongated implantable medical devices with reduced migration capabilities.

BACKGROUND

A wide variety of intracorporeal medical devices have been developed for medical use, for example, intravascular use. Some of these devices include guidewires, catheters, stents, and the like. These devices are manufactured by any one of a variety of different manufacturing methods and may be used according to any one of a variety of methods.

SUMMARY

This disclosure provides design, material, manufacturing method, and use alternatives for medical devices. An example medical device may include an implantable medical device that comprises:

a stent having a covered portion and an uncovered portion;

wherein the covered portion is releasably attached to the uncovered portion;

a cover member disposed along the covered portion;

wherein the uncovered portion includes a release tab that is designed to release the uncovered portion from the covered portion; and a removal member coupled to the covered portion for aiding in the removal of the covered portion from an implantation site.

Alternatively or additionally to any of the embodiments above, the covered portion of the stent includes a braid.

Alternatively or additionally to any of the embodiments above, the uncovered portion of the stent includes a crocheted wire.

Alternatively or additionally to any of the embodiments above, the uncovered portion of the stent is formed from a single wire.

Alternatively or additionally to any of the embodiments above, the uncovered portion of the stent is designed to permit tissue ingrowth therein so as to reduce migration of the stent.

Alternatively or additionally to any of the embodiments above, the covered portion, the uncovered portion, or both have a flared end region.

Alternatively or additionally to any of the embodiments above, proximally pulling the release tab unravels the uncovered portion of the stent.

Alternatively or additionally to any of the embodiments above, proximally pulling the release tab detaches the uncovered portion of the stent from the covered portion of the stent.

Alternatively or additionally to any of the embodiments above, the cover member is designed to substantially reduce tissue ingrowth along the covered portion of the stent.

Alternatively or additionally to any of the embodiments above, the uncovered portion of the stent includes a biodegradable material.

Alternatively or additionally to any of the embodiments above, the removal member includes a suture disposed about the covered portion of the stent.

An implantable medical device is disclosed. The implantable medical device comprises:

a stent having a braided portion and a crocheted portion;

wherein the braided portion is releasably attached to the crocheted portion; and a cover member disposed along the braided portion;

wherein the cover member is designed to limit tissue ingrowth along the braided portion; and wherein the crocheted portion of the stent is designed to permit tissue ingrowth therein so as to reduce migration of the stent.

Alternatively or additionally to any of the embodiments above, the crocheted portion of the stent is formed from a single wire.

Alternatively or additionally to any of the embodiments above, the braided portion, the crocheted portion, or both have a flared end region.

Alternatively or additionally to any of the embodiments above, a removal member is coupled to the braided portion for aiding in the removal of the braided portion from an implantation site.

Alternatively or additionally to any of the embodiments above, the crocheted portion includes a release tab and wherein proximally pulling the release tab unravels the crocheted portion of the stent and detaches the crocheted portion of the stent from the braided portion of the stent.

Alternatively or additionally to any of the embodiments above, the cover member is designed to substantially reduce tissue ingrowth along the braided portion of the stent.

Alternatively or additionally to any of the embodiments above, the crocheted portion of the stent is designed to permit tissue ingrowth therein so as to reduce migration of the stent.

Alternatively or additionally to any of the embodiments above, the crocheted portion of the stent includes a biodegradable material.

A method for removing an implantable medical device is disclosed. The method comprises:

engaging a release tab on a stent with a first removal member, the stent being implanted at an implant site;

wherein the stent includes:
a braided portion,
a crocheted portion releasably attached to the braided portion, and
a cover member disposed along the braided portion;

proximally retracting the release tab to unravel the crocheted portion and release the crocheted portion from the braided portion;

engaging a removal member on the braided portion of the stent with a second removal member; and removing the braided portion of the stent from the implant site.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
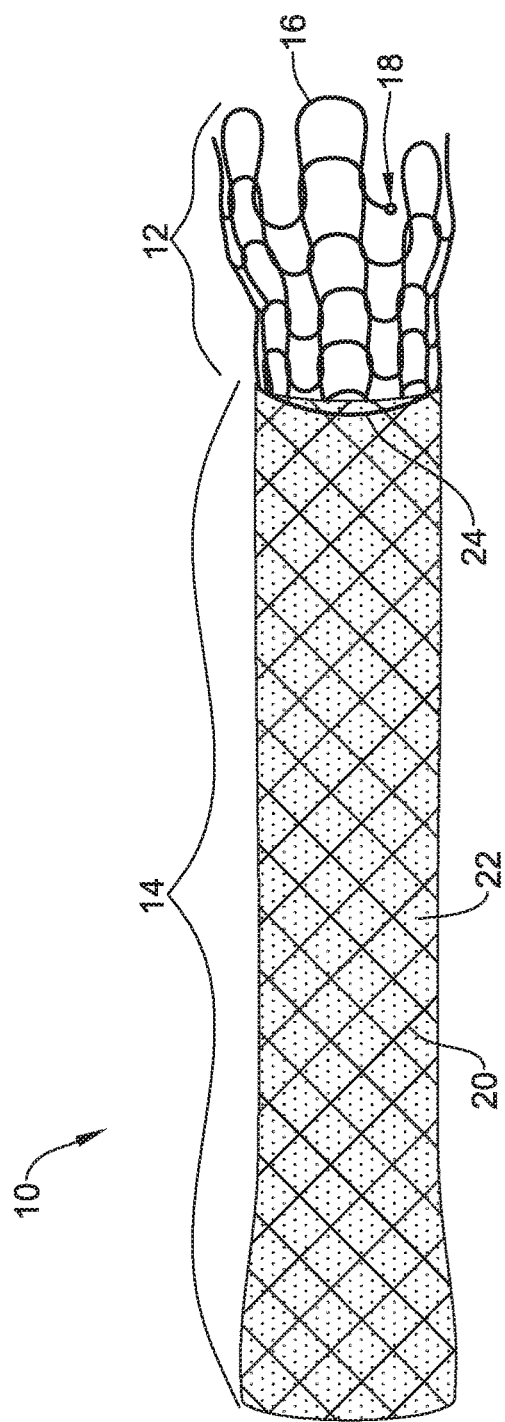
FIG. 1 is a side view of an example implantable medical device.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the disclosure.

FIG. 1 illustrates an example implantable medical device 10. Implantable medical device 10 may be configured to be positioned in a body lumen for a variety of medical applications. For example, implantable medical device 10 may be used to treat a stenosis in a blood vessel, used to maintain a fluid opening or pathway in the vascular, urinary, biliary, tracheobronchial, esophageal, or renal tracts, or position a device such as an artificial valve or filter within a body lumen, in some instances. In some instances, implantable medical device 10 may be a prosthetic graft, a stent-graft, or a stent (e.g., a vascular stent, tracheal stent, bronchial stent, esophageal stent, etc.), an aortic valve, filter, etc. Although illustrated as a stent, implantable medical device 10 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

In some circumstances, it may be desire to remove implantable medical device 10 from the body lumen. Some implantable stents may have an open, mesh-like configuration or braid that can be subject to tissue ingrowth. When tissue ingrowth occurs, it may be challenging to remove the stent. In order to reduce tissue ingrowth, a covering or sleeve may be disposed over the stent. While effective for reducing tissue ingrowth, the presence of the sleeve may allow the stent to migrate relative to the implantation target.

Implantable medical device 10 is designed to be efficiently removed, as needed, as well as to have anti-migration characteristics. For example, implantable medical device 10 may have a first section 12 and a second section 14. First section 12 and second section 14 are joined together as an expandable tubular framework with open ends and defining a lumen therethrough. First section 12 may be described as an uncovered section, a tissue ingrowth-promoting section, an anti-migration section, or the like. In other words, first section 12 may contribute to helping to keep implantable medical device 10 securely implanted at the target site. In some instances, first section 12 may be formed of a crocheted wire or filament, and thus be described as a crocheted section. Second section 14 may be described as a covered section, a tissue ingrowth-resistant section, a removable section, or the like. In some instances, second section 14 may be formed of a plurality of braided or interwoven wires or filaments, and thus be described as a braided section. Collectively, sections 12/14 work together to provide a number of desirable characteristics to implantable medical device 10.

First section 12 may be formed from a wire 16. Wire 16 may be a solid member of a round or non-round cross-section or may be tubular (e.g., with a round or non-round cross-sectional outer surface and/or round or non-round cross-sectional inner surface). In at least some instances, wire 16 is configured as a crocheted, generally cylindrical matrix that, upon the appropriate actuation, can be unraveled from a first configuration (e.g., cylindrical) to a second unraveled configuration (e.g., into a substantially "linear" configuration). In at least some instance, first section 12 may be formed from a singular wire 16. This may simplify the unraveling of wire 16. In order to aid shifting of wire 16 from the first configuration to the unraveled configuration, a release member or tab 18 may be disposed at end region of wire 16. Release tab 18 may be a portion of wire 16 that can be relatively easily grasped and pulled in order to unravel wire 16.

Second section 14 may include a braid or mesh 20. A cover member 22 may be disposed along braid 20. Cover member 22 may be designed to reduce tissue ingrowth. Accordingly, cover member 22 may allow second section 14 to be more easily removed from an implantation site at an appropriate time point. Cover member 22 may be formed from a suitable material. For example, cover member 22 may include silicone, polytetrafluoroethylene, polyurethane, or the like, or other materials including those disclosed herein. In some instances, cover member 22 is disposed along an outer surface of braid 20. In other instances, cover member 22 may be disposed along both an inner and an outer surface of braid 20. In some of these and in other instances, cover member 22 may encapsulate braid 20 or otherwise have braid 20 embedded therein. Coupling cover member 22 to braid 20 may include thermal bonding, molding, coating, dip coating, extruding, or the like. These are just examples.

In addition, second section 14 may also include a removal member 24. Removal member 24 may be disposed along second section 14 and may be utilized to partially collapse and/or otherwise aid in removal of second section 14. In some instance, removal member 24 may take the form of a suture that is disposed about an end region of braid 20 proximate first section 12. Removal member 24 may be disposed along the outer surface of braid 20, along the inner surface of braid 20, or may be intertwined with braid 20.

Removal member 24 may be generally designed so that pulling (e.g., proximally pulling) on removal member 24 may exert a radially inward force onto the end region of braid 20, effectively shifting braid 20 to a more conical or partially collapsed configuration, which may make it easier to remove implantable medical device 10 (e.g., second section 14). Sections 12/14 may be releasably secured to one another. For example, at the end of first section 12 adjacent to second section 14, first section 12 (e.g., wire 16) may include loops that extend through openings in braid 20. By doing so, first section 12 is secured to second section 14. When wire 16 is pulled so that first section 12 unravels, the loops in wire 16 may be pulled through braid 20 so as to detach first section 12 from second section 14. While a looped connection is shown, other connections are contemplated. For example, first section 12, or a portion thereof, may include a biodegradable material that is designed to dissolve or become bioabsorbed after a pre-determined amount of time. When this occurs, first section 12 is effectively released from second section 14. In other instances, first section 12 may be adhesively bonded to second section 14, for example.

One or both of sections 12,14 may be designed to shift between a first or "unexpanded" configuration and a second or "expanded" configuration. In at least some instances, one or both of sections 12,14 are formed from a shape memory material (e.g., a nickel-titanium alloy such as nitinol) that can be constrained in the unexpanded configuration, such as within a delivery sheath, during delivery and that self-expands to the expanded configuration when unconstrained, such as when deployed from a delivery sheath and/or when exposed to a pre-determined temperature conditions to facilitate expansion. In other instances, one or both of sections 12,14 may be designed to be actively expanded by a suitable expansion member or device such as, for example, a balloon. The precise material composition of sections 12,14 can vary, as desired, and may include the materials disclosed herein.

Figure 2:
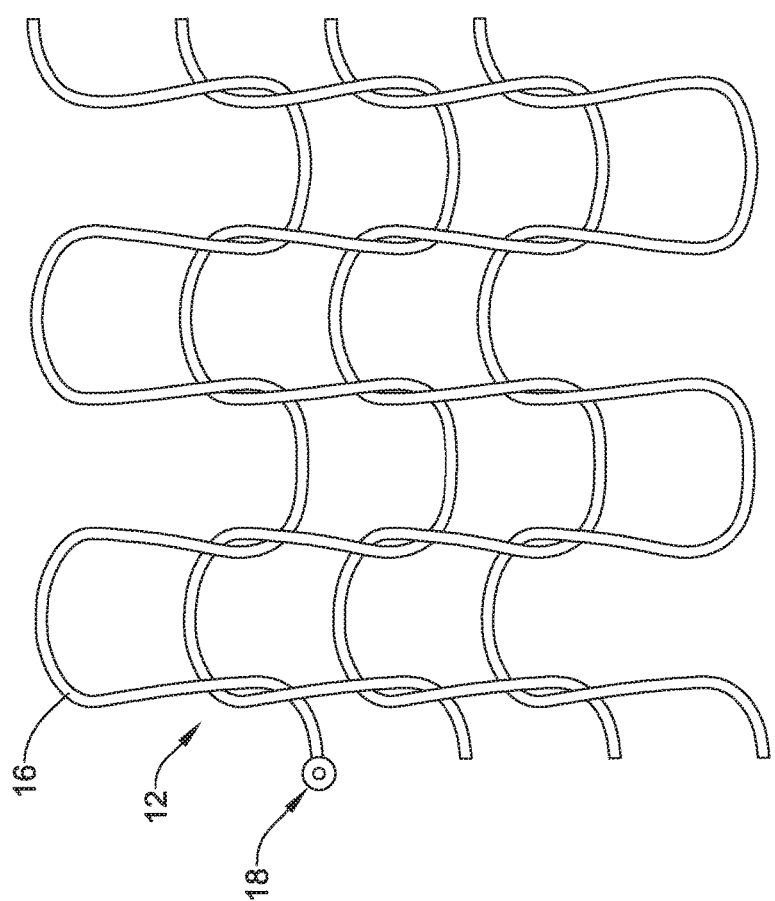
FIG. 2 illustrates a portion of an example implantable medical device.

FIG. 2 illustrates first section 12. In this implementation, first section 12 may be formed by looping or "crocheting" wire 16 into a desired configuration. The crocheted configuration of wire 16 may take the form of a series of loosely associated loops that are interconnected in a manner that allows wire 16 to maintain its integrity while in a cylindrical configuration, while also allowing for relatively easy unraveling by, for example, simply proximally pulling on release tab 18 (and/or on the end of wire 16 itself). In other words, the configuration of the loops of the crocheted wire 16 allows for wire 16 to be pulled (e.g., by grasping and pulling release tab 18) and unraveled. In addition, the looped framework of crocheted wire 16 may also define a series of openings that allow for tissue disposed along the surface of first section 12 to engage and grow within the openings. This may allow first section 12 to become secured with surrounding tissue in a manner that reduces the ability of implantable medical device 10 to migrate within a target body lumen.

In some implementations, first section 12 may include additional structural features that further aid in reducing migration of implantable medical device 10 within a target body lumen. For example, wire 16 may include a roughened surface that can frictionally engage the surface of the body lumen. In some instances, wire 16 may define a series of projections or "teeth" that can further engage tissue to resist migration of implantable medical device 10 in a body lumen. Additional implementations may include other structural features.

FIG. 2 also illustrates release tab 18. In at least some instances, release tab 18 may take the form of an enlarged, graspable region at the end of wire 16. The precise form of release tab 18 may vary. For example, release tab 18 may be a tab, loop, enlarged section, flattened section, droplet of a polymer or adhesive, etc.

Figure 3:
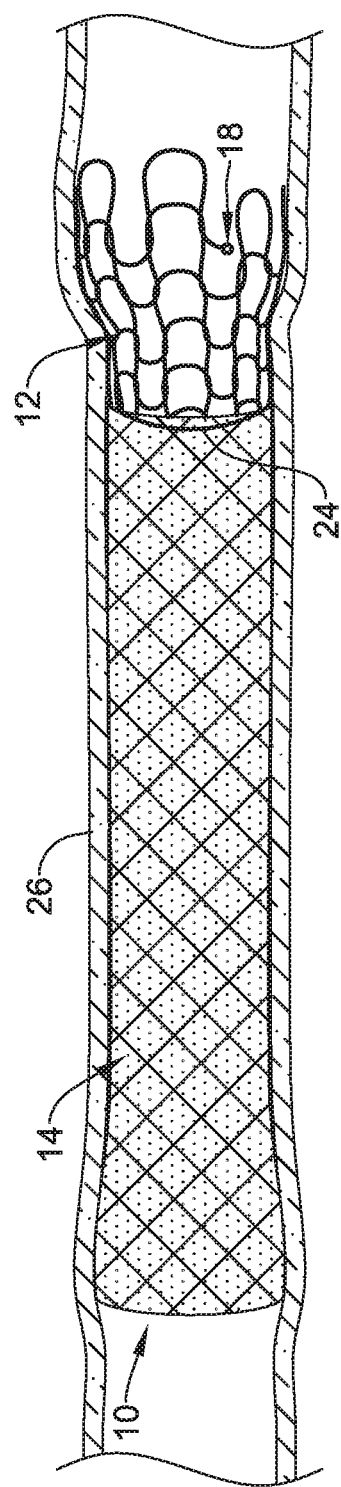
FIG. 3 illustrates an example implantable medical device implanted along a body lumen.

FIG. 3 illustrates implantable medical device 10 implanted along a body lumen 26. As disclosed herein, while implantable medical device 10 is implanted along body lumen 26, tissue ingrowth may occur along first section 12, which may reduce migration of implantable medical device 10 within body lumen 26. In some implementations, implantable medical device 10 may be removed from body lumen 26.

Figure 4:
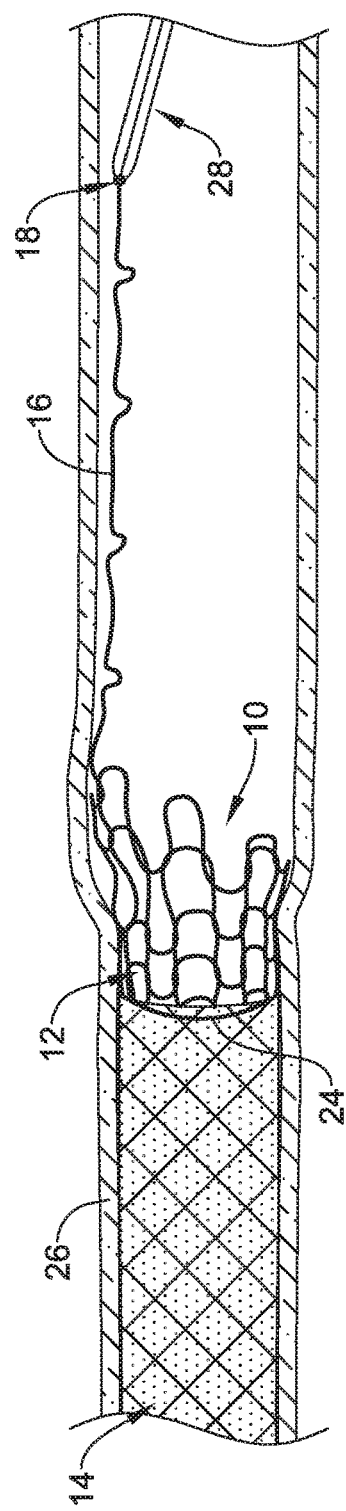
FIG. 4-5 illustrate a portion of a process for unraveling a section of an example implantable medical device.
Figure 5:
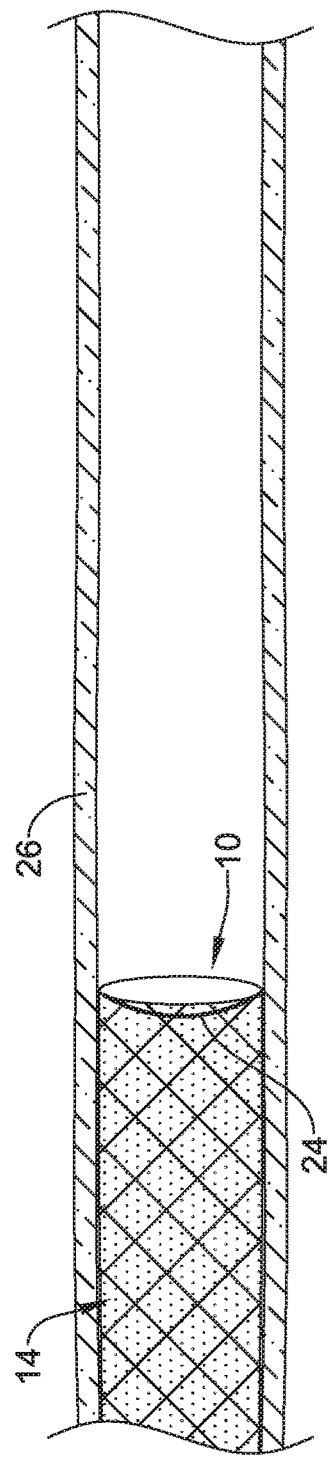

FIG. 4 illustrates a portion of a process for removing implantable medical device 10. For example, first removal member 28 may be used to grasp release tab 18. First removal member 28 may be proximally retracted until first section 12 unravels and is released from second section 14 as shown in FIG. 5. In order to do so, first section 12 may be unraveled, separated from second section 14, and removed from body lumen 26. For example, wire 16 of first section 12 may be pulled into an unraveled "linear" configuration that releases from second section 14. In instances where tissue ingrowth has occurred along first section 12, unraveling wire 16 may occur in a manner that allows wire 16 to be pulled from the ingrown tissue (e.g., in a manner similar to pulling a suture from a closed wound).

Figure 6:
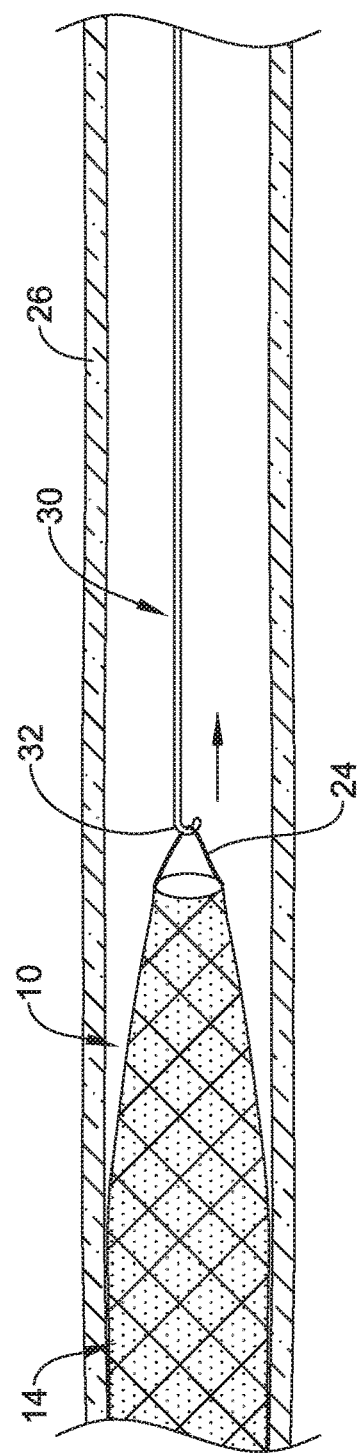
FIG. 6 illustrates a portion of a process for removing a section of an example implantable medical device from a body lumen.

Second removal member 30 may be used to remove second section 14 from body lumen 26 as shown in FIG. 6. For example, second removal member 30 may include a grasping section or hook 32 that engages removal member 24. Second removal member 30, which is schematically shown, may have a variety of forms suitable for engaging removal member 24. Removing second section 14 may include simply pulling second section 14 from the body lumen 26 (and, ultimately, the patient). Alternatively, a tubular removal or recapture device may be used. For example, second section 14 may be retracted into a tubular removal device and, subsequently, removed from body lumen 26.

The materials that can be used for the various components of implantable medical device 10 (and/or other devices disclosed herein) and the various tubular members disclosed herein may include those associated with medical devices. Implantable medical device 10, and/or the components thereof, may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 10 to achieve the same result. In some embodiments, a degree of Magnetic Resonance Imaging (MRI) compatibility is imparted into device 10. For example, device 10, or portions thereof, may be made of a material that does not substantially distort the image and create substantial artifacts (e.g., gaps in the image). Certain ferromagnetic materials, for example, may not be suitable because they may create artifacts in an MRI image. Device 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. An implantable medical device, comprising:
   a stent having a covered portion and an uncovered portion;
   wherein a proximal end of the covered portion is releasably attached to a distal end of the uncovered portion;
   a cover member disposed along the covered portion;
   wherein the uncovered portion includes a release tab that is designed to release the uncovered portion from the covered portion, wherein the release tab is disposed at a proximal end of the uncovered portion, wherein proximally pulling the release tab detaches the uncovered portion of the stent from the covered portion of the stent; and
   a removal member coupled to the covered portion for aiding in the removal of the covered portion from an implantation site.

2. The implantable medical device of claim 1, wherein the covered portion of the stent includes a braid.

3. The implantable medical device of claim 1, wherein the uncovered portion of the stent includes a crocheted wire.

4. The implantable medical device of claim 1, wherein the uncovered portion of the stent is formed from a single wire.

5. The implantable medical device of claim 1, wherein the uncovered portion of the stent is designed to permit tissue ingrowth therein so as to reduce migration of the stent.

6. The implantable medical device of claim 1, wherein the covered portion, the uncovered portion, or both have a flared end region.

7. The implantable medical device of claim 1, wherein the cover member is designed to substantially reduce tissue ingrowth along the covered portion of the stent.

8. The implantable medical device of claim 1, wherein the uncovered portion of the stent includes a biodegradable material.

9. The implantable medical device of claim 1, wherein the removal member includes a suture disposed about the covered portion of the stent.

10. An implantable medical device, comprising:
    a stent having a braided portion and a crocheted portion;
    wherein the braided portion is releasably attached to a first end region of the crocheted portion; and
    a cover member disposed along the braided portion;
    wherein the cover member is designed to limit tissue ingrowth along the braided portion;
    wherein the crocheted portion includes a release tab at a second end region of the crocheted portion opposite the first end region, and wherein pulling the release tab unravels the crocheted portion of the stent and detaches the crocheted portion of the stent from the braided portion of the stent; and
    wherein the crocheted portion of the stent is designed to permit tissue ingrowth therein so as to reduce migration of the stent.

11. The implantable medical device of claim 10, wherein the crocheted portion of the stent is formed from a single wire.

12. The implantable medical device of claim 10, wherein the braided portion, the crocheted portion, or both have a flared end region.

13. The implantable medical device of claim 10, wherein a removal member is coupled to the braided portion for aiding in the removal of the braided portion from an implantation site.

14. The implantable medical device of claim 10, wherein the crocheted portion of the stent includes a biodegradable material.

15. An implantable medical device, comprising:
    a stent having a covered portion extending to a first end of the stent, and an uncovered portion extending from the covered portion to a second end of the stent;
    wherein the uncovered portion of the stent is formed from a single crocheted wire having a plurality of loops for allowing tissue ingrowth therein;
    a cover member disposed along the covered portion to limit tissue ingrowth therein;
    a release tab located at a terminal end of the single crocheted wire at the second end of the stent, wherein the single crocheted wire forming the uncovered portion is configured to be unraveled via proximally pulling the release tab to remove the stent from a body lumen; wherein the covered portion comprises a plurality of braided wires forming a braded tubular member; and wherein the covered portion is releasably attached to the uncovered portion.

16. The implantable medical device of claim 15, further comprising a removal member coupled to the covered portion for aiding in the removal of the covered portion from a body lumen.

17. The implantable medical device of claim 15, wherein the crocheted wire extends through loops of the braided tubular member.

18. The implantable medical device of claim 15, wherein the uncovered portion comprises a biodegradable material configured to bioabsorbed to release the uncovered portion from the covered portion.

* * * * *